US010736606B2

(12) United States Patent
Michalski et al.

(10) Patent No.: US 10,736,606 B2
(45) Date of Patent: Aug. 11, 2020

(54) ACOUSTIC WINDOW LAYER FOR AN ULTRASOUND ARRAY (71) Applicant: KONINKLIJKE PHILIPS N.V., Eindhoven (NL)

(72) Inventors: Pawel Michalski, Eindhoven (NL); Franciscus Johannes Gerardus Hakkens, Eindhoven (NL); Edward Theodorus Maria Berben, Eindhoven (NL); Kevin Grayson Wickline, Eindhoven (NL); Lucas Johannes Anna Maria Beckers, Eindhoven (NL); Peter Dirksen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 264 days.

(21) Appl. No.: 15/774,611

(22) PCT Filed: Nov. 10, 2016

(86) PCT No.: PCT/EP2016/077244
§ 371 (c)(1),
(2) Date: May 9, 2018

(87) PCT Pub. No.: WO2017/081138
PCT Pub. Date: May 18, 2017

(65) Prior Publication Data
US 2018/0333136 A1    Nov. 22, 2018

Related U.S. Application Data
(60) Provisional application No. 62/253,484, filed on Nov. 10, 2015.

(30) Foreign Application Priority Data
Jan. 18, 2016  (EP) .................... 16151635

(51) Int. Cl.
*A61B 8/00*  (2006.01)
*G01S 15/89*  (2006.01)
(Continued)

(52) U.S. Cl.
CPC .......... *A61B 8/4483* (2013.01); *A61L 31/048* (2013.01); *A61L 31/049* (2013.01);
(Continued)

(58) Field of Classification Search
CPC ............... G10K 11/002; G01S 15/8938; G01S 7/52079; B06B 1/0207; B06B 1/0292; A61L 31/049; A61L 31/048; A61B 8/4483
(Continued)

(56) References Cited
U.S. PATENT DOCUMENTS 4,079,099 A   3/1978  Gergen et al.
4,699,150 A   10/1987 Kawabuchi et al.
(Continued)

FOREIGN PATENT DOCUMENTS

CN    104226577 A    12/2014
WO    2014013735     1/2014

*Primary Examiner* — Thomas Truong (57) ABSTRACT

An acoustic window layer for an ultrasound array, which layer has an inner surface arranged to face the array and an outer surface arranged to face a patient, and comprising an outer layer comprising a thermoplastic polymer selected from a polyolefin family (TPO) and an elastomer selected from the polyolefin family (POE) blended therein, wherein the outer layer located at the outer surface of the acoustic window layer. In a preferred embodiment the blend comprises a copolymer of ethylene-octene and polymethylpentene. The thermoplastic polyolefin provides the blend with mechanical, chemical stability and low acoustic wave attenuation; whilst the polyolefin elastomer provides a pos-
(Continued)

sibility to tune the acoustic impedance of the blend and to further improve its acoustic wave propagation properties.

15 Claims, 5 Drawing Sheets

(51) Int. Cl.
  *B06B 1/02* (2006.01)
  *G10K 11/00* (2006.01)
  *A61L 31/04* (2006.01)
  *G01S 7/52* (2006.01)
(52) U.S. Cl.
  CPC .......... *B06B 1/0207* (2013.01); *B06B 1/0292* (2013.01); *G01S 7/52079* (2013.01); *G01S 15/8938* (2013.01); *G10K 11/002* (2013.01)
(58) Field of Classification Search
  USPC ........................................ 310/300, 309, 310
  See application file for complete search history.

(56) References Cited

U.S. PATENT DOCUMENTS

| | | |
|---|---|---|
| 4,820,753 A | 4/1989 | Caprette et al. |
| 9,144,421 B1 | 9/2015 | Lau et al. |
| 10,013,969 B2 | 7/2018 | Li et al. |
| 2013/0301394 A1* | 11/2013 | Chen .................... B06B 1/0292 367/155 |

* cited by examiner

ACOUSTIC WINDOW LAYER FOR AN ULTRASOUND ARRAY

This application is the U.S. National Phase application under 35 U.S.C. § 371 of International Application No. PCT/EP2016/077244, filed on Nov. 10, 2016, which claims the benefit of Provisional Application Ser. No. 62/253,484 filed Nov. 10, 2015 and EP Application Serial No. 16151635.6, filed Jan. 18, 2016. These applications are hereby incorporated by reference herein.

FIELD OF THE INVENTION

The invention relates to an acoustic window layer for an ultrasound array having an inner surface arranged to face the array and an outer surface arranged to face a patient.

The invention further relates an ultrasound probe comprising such an acoustic window layer.

BACKGROUND OF THE INVENTION

Ultrasound transmitting components, such as acoustic windows and lenses, for medical imaging systems are desired to comply with several requirements, such as providing: an optimal low loss acoustic wave transmission; chemical and mechanical barriers to protect the ultrasound array elements; electrical barrier to protect a patient from the electrically active transducer elements. In U.S. Pat. No. 4,699,150 polymethylpentene polymer (for example available from Mitsui Chemicals under trade name TPX) is used as a contact member, which is brought to contact with an object being examined and formed on the one surface of the ultrasound transducer. The polymethylpentene polymer is chosen due to its durability and low acoustic wave attenuation.

However, polymethylpentene based polymers used as a part of acoustic windows and lenses in the ultrasound imaging systems introduce image artifacts. Furthermore, polymethylpentene based polymers have an acoustic impedance of 1.7 MRayls or higher, which is too high for some of the medical ultrasound applications. There are alternative materials as for example: polyether/polyamide block copolymer which has low attenuation but low chemical compatibility, and filled silicone (silicon rubber) which has higher attenuation and fluid permeability issues.

Currently there is no available as acoustic windows material, which would meet most of the ultrasound system's requirements.

SUMMARY OF THE INVENTION

It is an object of the present invention to provide an acoustic window layer for an ultrasound array of the kind set forth in the opening paragraph which provides improved acoustic wave propagation combined with chemical and mechanical stability of the layer.

This object is achieved according to the invention by providing an outer layer comprising a thermoplastic polymer polymethylpentene and an elastomer selected from the polyolefin family (POE) blended therein, wherein the outer layer located at the outer surface of the acoustic window layer.

An introduction of the polyolefin elastomer into the blend with the thermoplastic polyolefin polymer, such as polymethylpentene, changes the density of the blend. Since acoustic impedance of a material is proportional to the density of this material, the average impedance of the outer layer may be tuned with the blended elastomer therein. The thermoplastic polyolefin provides the blend mechanical, chemical stability and with low acoustic wave attenuation; whilst the polyolefin elastomer provides a possibility to tune the acoustic impedance of the blend and to further improve its acoustic wave propagation properties. If the outer layer exhibits a low acoustic attenuation and reduced acoustic impedance that may be closer matched to the body, human tissue (about 1.6 MRayl). In addition the outer layer comprising the polyolefin nature of the blend provides low water permeation levels. An outer layer comprising this blend is resistant to disinfectants (used for typical medical ultrasound equipment); and has a good mechanical protective properties as impact and wear resistance and is bio compatible. The blend of the thermoplastic polyolefin and polyolefin elastomer also provides an increased shear wave attenuation that beneficially reduces a cross talk between the transducer elements. Therefore, an application of the acoustic window layer comprising a blend of the polyolefin thermoplastic polymer and elastomer shows a reduction of image artefacts during the ultrasound imaging. Polymethylpentene (TPX) material shows one of the lowest longitudinal acoustic wave attenuation among the thermoplastic polyolefins. It shows an acoustic loss per millimeter for acoustic energy passing therethrough of less than 3.5 dB for a wide range of the acoustic wave frequencies applicable in medical ultrasound, such as 2 to 10 MHz. Polymethylpentene is suitable for blending with polyolefin elastomers having higher attenuation for both the longitudinal acoustic wave and share wave.

In another embodiment of the present invention the polyolefin elastomer is a copolymer. In yet another embodiment the elastomer is a thermoplastic elastomer comprising copolymer chains.

The outer acoustic layer of this embodiment would be a blend having thermoplastic properties. An example of the thermoplastic polyolefin elastomer (TPE) may be a copolymer of ethylene and another alpha olefin, such as octane or butane. The resulting blend of the TPX and ethylene-octene copolymer inherits from the TPX the reduced density with relatively high acoustic wave velocity; and from the copolymer reduced acoustic impedance and increased shear wave attenuation.

In yet further embodiment the outer layer has a density in between 0.8 and 0.85 $g/cm^3$ and acoustic wave velocity in between 2000 and 1900 mm/msec.

It is desirable to provide an acoustic lens having a higher acoustic wave velocity for real-time ultrasound imaging. In addition, in order to avoid acoustic wave scattering at the interface of the lens with a tissue due to an impedance miss-match it is further desired to provide the outer layer with an acoustic impedance closer to that of the tissue. The resulting blend possessing a relatively low density 0.8 and 0.85 $g/cm^3$ and showing acoustic wave velocity in between 2000 and 1900 mm/msec, provides better image quality, when used in the probe.

In another embodiment of the present invention the outer layer exhibits a first melting point in between 30 and 70 centigrade Celsius and a second melting point in between 200 and 250 centigrade Celsius.

The first melting point in the range between 30 and 70 centigrade Celsius corresponds to the polyolefin elastomer forming the blend, while the second melting point in the range between 200 and 250 centigrade Celsius is melting point of the thermoplastic polyolefin forming the blend. The presence of two distinct melting points is an indication that the outer layer comprises a blend of two materials providing the outer layer with an optimal acoustic energy transmission combined with thermoplastic and elastic properties.

In another embodiment of the present invention the outer layer exhibits a first glass transition temperature below −40 centigrade Celsius and a second glass transition temperature in between 0 and 50 centigrade Celsius.

Glass transition temperature is a property of polymer materials. The glass transition temperature (Tg) is the temperature at which an amorphous polymer becomes soft upon heating or brittle upon cooling. The outer layer comprising the blend of the thermoplastic polyolefin and the polyolefin elastomer can be characterized by two glass transition temperatures, one of which below −40 centigrade Celsius corresponds to the elastomer blended in the thermoplastic polymer, while glass transition temperature in between 0 and 50 centigrade Celsius corresponds to the thermoplastic polyolefin itself.

In yet another embodiment of the present invention the acoustic window layer further comprises an inner layer located at the inner surface of the acoustic window layer, wherein the inner layer comprises a thermoset rubber, such as polybutadiene.

The benefit of the acoustic window layer comprising the thermoset rubber is especially pronounced for the CMUT arrays. The relatively light molecular weight of the rubber combined with its relatively low hardness (below 60 ShoreA, preferably below 50 ShoreA) may provide an improved acoustic contact between the acoustic window layer and the CMUT's membrane adapted to vibrate. In addition, the low acoustic wave attenuation of the thermoset rubber combined with the chemical and mechanical stability of the outer layer may provide an improved transition of the acoustic wave throughout the acoustic window layer. Polybutadiene shows one of the lowest attenuation effects on the propagating acoustic energy. This material provides a large band width of about 140% at 3 dB-point for the propagating acoustic signal.

These and other aspects of the invention will be apparent from and elucidated with reference to the embodiments described hereinafter.

DETAILED DESCRIPTION OF EMBODIMENTS

Figure 1:
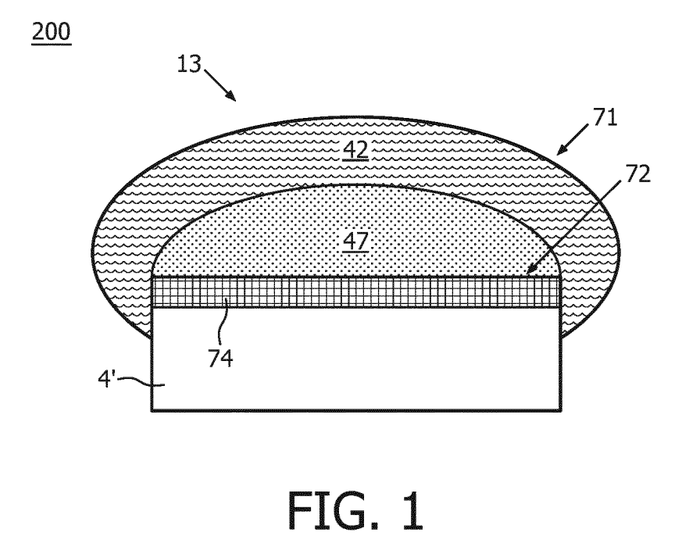
FIG. 1 shows schematically and exemplarily side view of an ultrasound probe comprising an ultrasound array and an acoustic window layer having an outer layer and inner layer in accordance with the principles of the invention.
Figure 8:
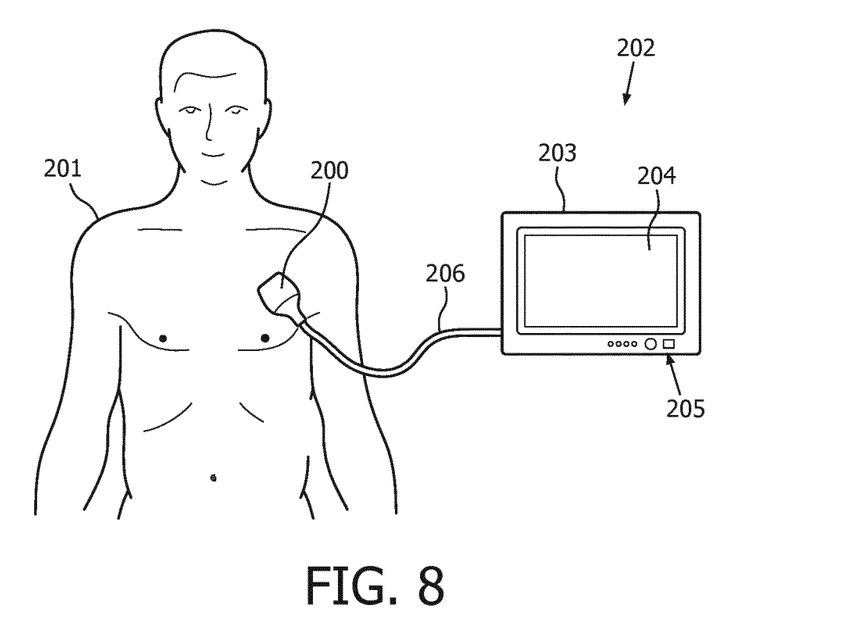
FIG. 8 shows a schematic illustration of an embodiment of an ultrasound imaging system.

FIG. 1 shows schematically and exemplarily an embodiment of an ultrasound probe 200 according to the invention, comprising an ultrasound array 74. The ultrasound array 74 has an ultrasound wave emitting side facing an inner surface 72 of an acoustic window layer 13 and a backing side opposite to the emitting side. The ultrasound array may contain ultrasound transducers coupled to an integrated circuitry adapted to drive and control the transducers in the array. The backing side of the array is electrically coupled to a probe's base 4', which communicates input and output signals of the integrated circuitry to and from an ultrasound system 202 (FIG. 8).

The acoustic window layer 13 comprises an outer layer 42 located at an outer surface of the acoustic window layer 13. The outer surface is intended to face a patient 201 or a body to be examined by the ultrasound imaging system 202. The outer layer 42 comprises a blend of a thermoplastic polymer selected from a polyolefin family (thermoplastic polyolefin or TPO) and an elastomer selected from a polyolefin family (polyolefin elastomer or POE).

Most of Eastomers are thermoset elastomers, which are generally characterized by wide-meshed crosslinking of the "knotted" molecular chains. This type of crosslinking means that the materials have a high level of dimensional stability but are still elastically malleable. By applying load (for instance tensile load) the chains become stretched, but after removal of the load they relax again. A typical hardness of the uncured elastomers is below 50 ShoreA, measured by a durometer (A scale). An olefin family (also alkenes) is a family of the unsaturated hydrocarbons comprising at least one carbon-carbon double bond. A polyolefin is a polymer comprising monomers selected from the olefin family.

Thermoplastic polymers are polymers in which, unlike thermoset elastomers, the molecular chains are not crosslinked. They consequently demonstrate plastic elastic behavior and are thermoformable (having the property of softening or fusing when heated and of hardening again when cooled). This formability is reversible, in other words can be repeated as often as required as long as the material is not thermally damaged by overheating. Since thermoplastics have little or no cross-linking their individual polymer chains can slip past one another on heating. In thermoplastic polyolefin, compared to the saturated hydrocarbons, the polyolefin family provides the thermoplastic polymer with a relatively light molecular weight, here it is assumed that the thermoplastic polymer does not further contain oxygen comprising functional groups. The thermoplastic polyolefin comprises linear isotactic polymers. In general thermoplastic polymers have a hardness of above 60 ShoreA.

Another type of elastomers is a thermoplastic elastomers (TPEs), which are as well as general thermoplastics mentioned above have no or little crosslinking. The thermoplastic elastomers can be copolymers, wherein the high level of thermoplastic elastomer dimensional stability and their elastic malleability is achieved by combining in one two different types of polymers. TPEs provide a material with an ability to be stretched to moderate elongations and return to its near original shape creating a longer life and better physical range. Most commercially available TPEs are polyolefin copolymers of either ethylene-butene or ethylene-octene.

It has been discovered that the introduction of the polyolefin elastomer into the blend of the polyolefin thermoplastic polymer used for the outer layer 42 provides an increased shear wave attenuation that beneficially reduces a cross talk between the transducer elements in the array 74. Therefore, the ultrasound probe 200 having the acoustic window layer 13 with the outer layer 42 formed from a blend of the thermoplastic polyolefin and polyolefin elastomer shows a reduction of image artefacts during the ultrasound imaging.

Blending (compounding) of these polymer materials can, for instance, be performed with a twin screw extruder. The blend of the thermoplastic polymer and the elastomer represents a so called immiscible polymer blends (heterogeneous polymer blends), wherein the blend made of these two polymers exhibits two sets of distinct physical properties, such as glass transition temperatures and melting point, corresponding to the materials forming the blend. An additional advantage of the polyolefin elastomer that it is compatible with most olefinic materials, where in olefinic is any of a class of unsaturated open-chain hydrocarbons having at least one double bond. It shall be noted that blending provides a homogenous distribution of the thermoplastic and elastomer materials within a given volume, without a formation of separate islands of different materials, wherein said islands can introduce additional sources of scattering for the ultrasound waves.

An introduction of the polyolefin elastomer into the blend with thermoplastic polyolefin changes the density of the blend compared to the pure thermoplastic. And since acoustic impedance (Z) is defined as the product of acoustic propagation velocity (v) for acoustic energy (or wave) in a medium and density (ρ) of this medium:

$$Z = \rho * v,$$

the acoustic impedance of the outer layer can be beneficially adjusted to the a soft tissue's impedance, which is about 1.6 MRayl. In the meantime other acoustic properties of the outer layer, such as acoustic wave velocity, acoustic energy attenuation and shear wave attenuation, can be also tuned by selecting a different ratio of the elastomer content blended in the thermoplastic polymer. It is desirable to use thermoplastic polyolefin at the outer layer, which can provide mechanical robustness without circumventing ultrasound image quality, which in addition has acoustic impedance closer to the soft tissue impedance and shows increased acoustic wave velocity.

One of the preferred materials for the thermoplastic polymers used in the outer layer is polymethylpentene (poly 4-methyl pentene-1). Polymethylpentene (available from Mitsui under trade name is TPX) material shows a low longitudinal acoustic attenuation as can be seen from FIG. 3 curve 83. In this context the longitudinal attenuation corresponds to the wave's amplitude reduction while propagating from the inner surface arranged to face the array the outer surface. In the frequency range from 0 up to 10 MHz, the polymethylpentene layer shows the attenuation value below 3 dB/mm.

In a further example, the polymethylpentene material is blended with a copolymer forming the polyolefin elastomer. Copolymers are a physical mix of polymers (two different monomers) which consist of materials with different elastic properties. The copolymer of the polyolefin elastomer is a copolymer of ethylene and alpha olefin such as octane or butane. Alpha-olefins (or α-olefins) are a family of organic compounds which are alkenes with a chemical formula $CnH_{2n}$, distinguished by having a double bond at the primary or alpha (a) position. In another embodiment, the outer layer comprises a blend of polymethylpentene and ethylene-octene copolymer. This copolymer is available from Dow Chemical under trade name Engage.

The layer of polymethylpentene (TPX) shows the lowest acoustic attenuation among the materials listed in the table. Another advantage of the TPX is that this material has relatively low density, while due to its hardness exhibiting relatively high acoustic wave velocity (above 2 mm/msec). Compared to other more dense polymers with similar acoustic wave velocities, the TPX has relatively high acoustic wave velocity, while showing relatively low acoustic impedance. However, as has been already indicated above that the TPX material has low shear wave attenuation. In contrast to the emitted ultrasound waves propagating from the ultrasound array throughout the acoustic window layer 13 towards the patent, the shear wave travels along the acoustic window surface and increases the cross talk between the transducers affecting the ultrasound image quality.

The ethylene-octene copolymer being a thermoplastic elastomer is suitable for blending with polymethylpentene due to its olefin nature. This copolymer exhibits on average lower, than the TPX, acoustic impedance and almost an order of magnitude higher shear wave attenuation. The resulting blend of the TPX and ethylene-octene copolymer inherits from the TPX the reduced density with relatively high acoustic wave velocity; and from the copolymer reduced acoustic impedance and increased shear wave attenuation. Therefore, an improved outer layer 42 comprising the blend from the TPX and the ethylene-octene copolymer can be obtained. This blend provides the window layer of the acoustic probe with durability and low acoustic attenuation properties next to the improved imaging quality due to the reduced image artifacts originating from the window layer.

Table 1 shows a comparison of the acoustic properties measured for different materials: polymethylpentene (Mitsui TPX MX0002, having 4 monomers in a polymer chain), polyolefin elastomer (Engage 8180 having 4 monomers in a polymer chain); two blends of the polymethylpentene (TPX MX0002) and polyolefin elastomer (Engage 8180), wherein an amount of the elastomer in the blend 15% and 20% of total blend's weight correspondingly

TABLE 1

Changes in material's parameters of different layer materials: density, acoustic wave velocity, acoustic impedance, acoustic energy attenuation (at the acoustic wave frequency of 7 MHz) and shear wave attenuation.

| Layer material | Density (g/cm$^3$) | Velocity (mm/msec) | Impedance (MRayl) | Attenuation @7 MHz (dB/mm) | Shear wave Attenuation (dB/mm) |
| --- | --- | --- | --- | --- | --- |
| Engage 8180 | 0.874 | 1622 | 1.417 | 4.51 | >17 |
| TPX/Engage (15%) | 0.835 | 1923 | 1.607 | 2.71 | 5 |
| TPX/Engage (20%) | 0.832 | 1899 | 1.580 | 3.12 | 10 |
| TPX | 0.819 | 2067 | 1.692 | 2.31 | 1 |

Engage 8180 has the lowest density from the commercially available Engage types. Engage 8180 material shows a considerable attenuation of the shear wave (above 17 dB/mm) in addition it also shows the relatively high acoustic wave attenuation increasing from about 1.5 dB/mm at 2.5 MHz up to 5 dB/mm at 7.5 MHz. The blend of TPX and Engage 8180, wherein a weight ratio of 85% and 15% correspondingly, compared to the TPX, shows a slight increase in density up to 0.835 gram per cubic centimeter (g/cm$^3$) with an improved shear wave attenuation of about 5 dB/mm and an increased acoustic wave attenuation being about 2.71 dB/mm at 7.5 MHz. The acoustic impedance of the TPX and Engage 8180 (85/15%) blend is reduced down to 1.6 MRayl, compared to the TPX material, which brings acoustic impedance value of the outer layer 42 closer to the tissue impedance. The share wave attenuation of the blend can be further improved (increased) by increasing the weight ratio of the Engage in the blend. In case of the blend of TPX and Engage 8180, with the corresponding weight ratio of 80% and 20%, the shear wave attenuation may be as high as 10 dB/mm with the acoustic impedance further reduced to 1.58 MRayl. These improvements may be balanced by a slight increase in the acoustic wave attenuation energy value of about 3.12 dB/mm at 7 MHz.

The blending of these polymers provides a freedom of varying the acoustic wave velocity of the blend by changing the weight ratio of the polymers in the blend depending on different medical applications.

Figure 3:
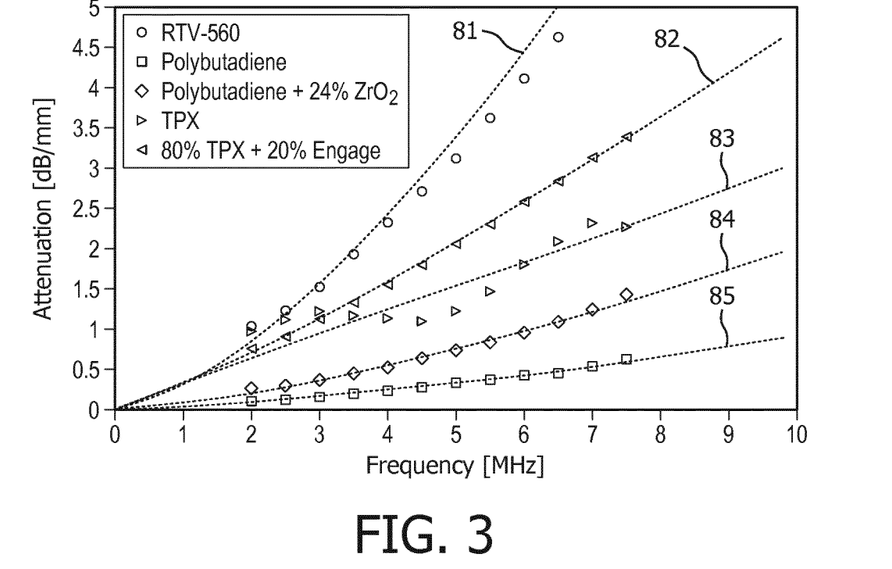
FIG. 3 is a graph comparing an acoustic frequency dependence of an acoustic loss (in dB) per millimeter for acoustic energy passing therethrough for different acoustic window materials.

FIG. 3 shows an acoustic frequency dependence of attenuation of the acoustic energy passing therethrough for different acoustic window materials. Symbols indicate measured data and lines indicate simulated dependencies. The presented materials show a steady increase of the attenuation value with the increase in frequency. The highest attenuation, which increases considerably with the frequency, is observed for the commonly used filled silicon rubber (RTV-560, curve 81): the attenuation reaches almost 5 dB/mm at a frequency around 7 MHz. The smallest attenuation is observed for polybutadiene (curve 85), which shows attenuation below 1 dB/mm at frequencies below 10 MHz. Compared to the RTV-560 the polymethylpentene material (TPX, curve 83) shows an improved attenuation varying from about 0.5 dB/mm at 2 MHz up to 3 dB/mm at 10 MHz. The blend of the TPX and Engage 8180 in the weight ratio of 80% and 20% shows an increased attenuation dependency compared to the pure polymethylpentene, however, this dependency is still improved compared to the commonly used filled silicon. The acoustic wave attenuation in the TPX/Engage 8180 (20%) blend changes from about 0.5 dB/mm at 2 MHz up to 4.5 dB/mm at 10 MHz. Thus, the outer layer formed from blend of thermoplastic olefin (polymethylpentene) and polyolefin elastomer (ethylene-octene copolymer) exhibits a low acoustic attenuation and reduced acoustic impedance that may be closer matched to the body/human tissue. In addition the outer layer has low water permeation levels; is resistant to disinfectants (used for typical medical ultrasound equipment); and has a good mechanical protective properties as impact and wear resistance and is bio compatible.

Due to the fact that both components forming the blend are olefin based the material of the outer layer is non-polar; thus, chemically stable towards the disinfectant treatment commonly used for medical devices.

Suitable ultrasound transducers for use in the ultrasound array 74 may be known to the skilled person ultrasound transducers, such as PZTs or CMUTs.

Figure 4:
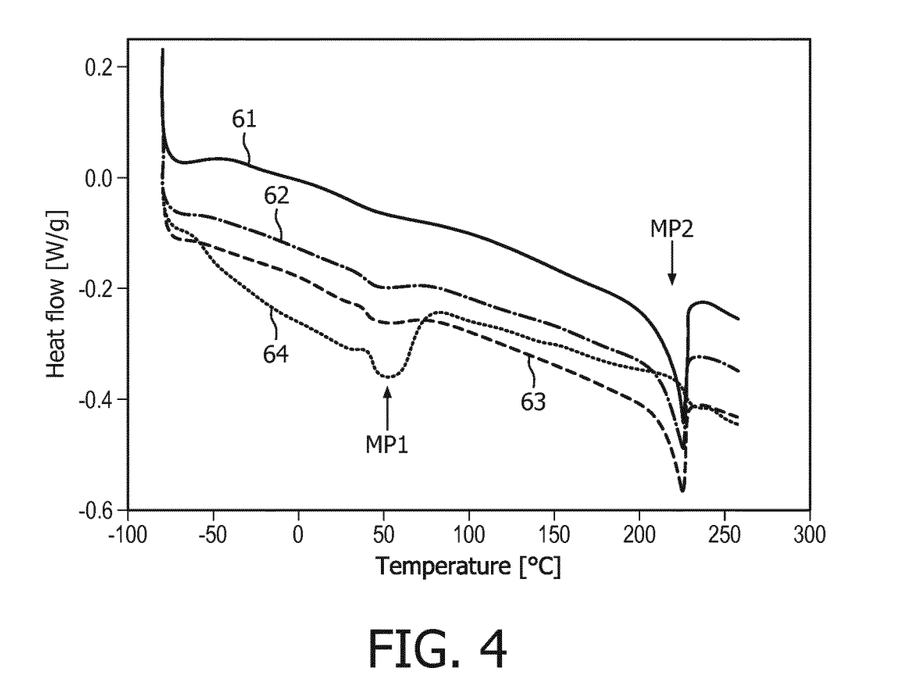
FIG. 4 shows comparison between the differential scanning calorimetry curves for polymethylpentene, polyolefin elastomer and different concentration blends of polymethylpentene with polyolefin elastomer.

In order to characterize the obtained blends in accordance to the present invention the differential scanning calorimetry and dynamic mechanical analyses were performed. FIG. 4 shows the differential scanning calorimetry curves for polymethylpentene (TPX MX0002, curve 61); polymethylpentene/polyolefin elastomer blends (TPX/Engage 8180) having the weight ratio of 80%/20% (curve 62) and 85%/15% (curve 63) correspondingly; and polyolefin elastomer (Engage 8180, curve 64).

As can be seen from the curves 62 and 63, the heat flow temperature dependence has two extreme points around 50 and 225 centigrade Celsius. This indicates that the blend of the polymethylpentene with the polyolefin elastomer exhibits two melting points, wherein the lowest temperature point represents a first melting point (MP1) in between 30 and 70 centigrade Celsius associated with the polyolefin elastomer (compared to the curve 64) and the highest point represents a second melting point (MP2) in between 200 and 250 centigrade Celsius associated with the thermoplastic polymer (compared to the curve 61). Indeed, heat flow curves of pure Engage 64 and TPX 61 have one extreme point each: around 50 centigrade Celsius corresponding to the polyolefin elastomer (Engage, 64) and around 225 centigrade Celsius corresponding to thermoplastic polymer (TPX, 61).

Figure 5:
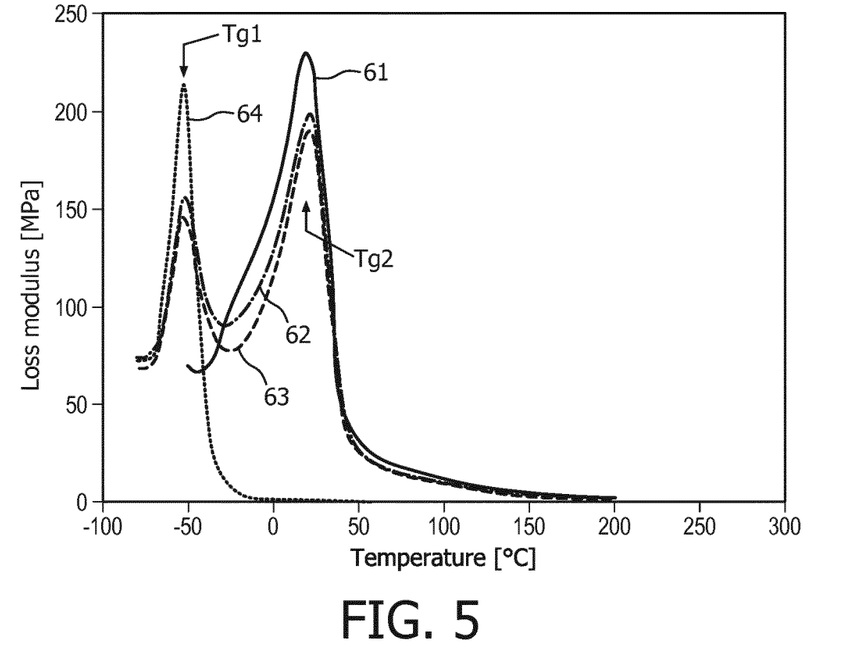
FIG. 5 shows comparison between the dynamic mechanical analyses curves for polymenthylpentene, polyolefin elastomer and different concentration blends of polymethylpentene with polyolefin elastomer.

FIG. 5 shows the dynamic mechanical analyses curves for the same set of materials. For simplification the same reference numbers are used in both figures: FIG. 4 and FIG. 5. The loss modulus temperature dependence of the blends (curves 63 and 63) shows two extreme combining the properties of both blended materials. The maximum below −40 centigrade Celsius, in particular around −60 centigrade Celsius, is a first glass transition temperature (Tg1) corresponding to the polyolefin elastomer, in particular Engage. The maximum between 0 and 50 centigrade Celsius, in particular around 25 centigrade Celsius, is a second glass transition temperature (Tg2) corresponding to the thermoplastic polyolefin, in particular TPX. The loss modulus curves of pure Engage 64 and TPX 61 have one extreme point each: around −60 centigrade Celsius corresponding to the elastomer (Engage, 64) and around 25 centigrade Celsius corresponding to thermoplastic polyolefin (TPX, 61).

The acoustic window layer of the embodiment may comprise an inner layer 47, as shown in FIG. 1, located at the inner surface 72 of the acoustic window layer 13. The material(s) forming the inner layer 47 can be selected based on the acoustic requirement of the ultrasound transducers, such as their acoustic impedance and mechanism of the electro-acoustical transformation. The inner layer 47 provides an acoustic coupling of the emitting surface of the ultrasound array to the acoustic window layer 13.

Figure 2:
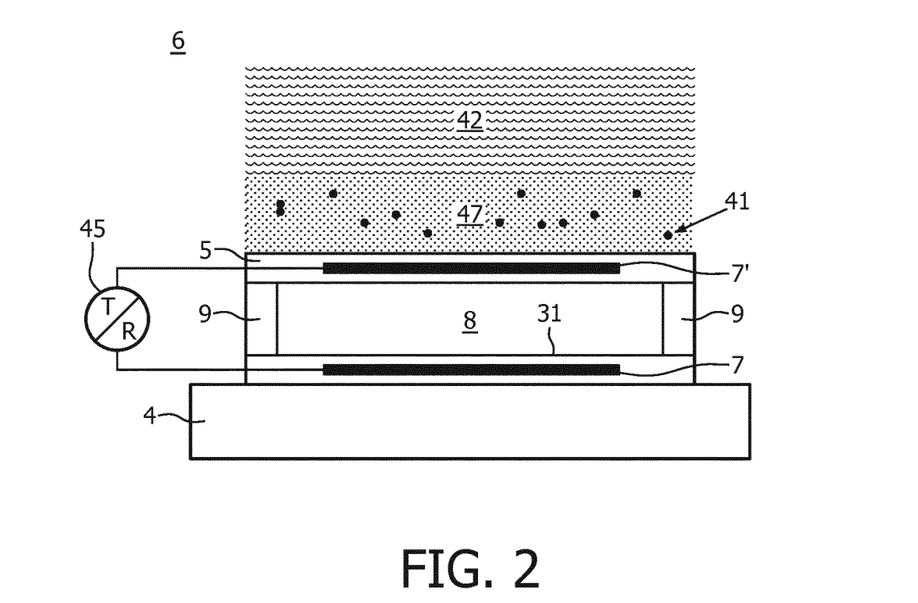
FIG. 2 shows schematically and exemplarily a side view of a CMUT cell of the ultrasound array and an overlaying acoustic window layer having the inner layer and the outer layer located at the outer surface side of the acoustic window layer.

In another embodiment of the present invention the ultrasound array 74 comprises at least one CMUT cell as shown in FIG. 2. Such CMUT cell is typically fabricated on a substrate 4, such as a silicon wafer. This substrate may be located within the base 4' of the probe 200 in FIG. 1. An ultrasound array 74 of an ultrasound probe 200 may comprise one or more CMUT cells 6. The CMUT cells may be either individually activated or in combination with each other. The individual cells can have round, rectangular, hexagon or other peripheral shapes.

Each CMUT cell has at least a pair of electrodes 7' and 7 separated by a cavity 8. The cavity 8 is formed in between a membrane 5 that is suspended over a cell floor 31 formed by the top surface of the substrate 4. The membrane 5 may be made of silicon nitride and is adapted to move or vibrate. It can be suspended over the cell floor 31 (or substrate) through a plurality of supporting portions 9 (in FIG. 2 two supporting portions 9 are shown). The electrodes 7, 7' are made of electrically conductive material, such as metal. The bottom electrodes 7 may be embedded in the floor of the cell 31, while the top electrode 7' may be embedded in the membrane 5. The electrode 7 and 7' may be also deposited on the cell floor 31 or the membrane 5 as additional layers. The bottom electrode 7 is typically insulated on its cavity-facing surface with an additional layer (not shown). This insulating layer can comprise either one of or a combination of an oxide-nitride-oxide (ONO) dielectric layer, silicon oxide layer, aluminium or hafnium oxide layers. The insulating layer may be formed above the bottom electrode 7 and below the membrane electrode 7'. The ONO-dielectric layer advantageously reduces charge accumulation on the electrodes which leads to device instability, drift and reduction in acoustic output pressure. The supporting portions 9 may be made of an insulating material such as silicon oxide or silicon nitride. The cavity 8 can be either air- or gas-filled, or wholly or partially evacuated. Two electrodes 7 and 7' separated by the cavity 8 represent a capacitance. An application of electrical signal through a drive circuit 45 coupled to the electrodes 7 and 7' causes a mechanical movement/vibration of the membrane 5, which results in the change of the capacitance and can be manipulated by an associated with the CMUT transducer integrated circuitry. The drive circuit 45 can be implemented as an integrated part of the integrated circuitry of the ultrasound array. The drive circuit 45 usually comprises an a.c. signal voltage and a d.c. voltage sources and associated to these sources circuitry.

In order to provide an optimal acoustic coupling of the inner layer 47 to the CMUt membrane 5, the inner layer 47 may comprises one or more materials selected from thermoset rubbers. The thermoset rubbers are polymeric materials which contain only hydrogen and carbon atoms and have a relatively low density (below 1 g/cm$^3$).

For example, the inner layer 47 material can comprise polybutadiene or butyl rubber. Butyl rubber is an isobutylene-isoprene copolymer and shows hardness as low as 40 ShoreA.

Polybutadiene belongs to the thermoset rubbers containing no other atom types than hydrogen and carbon. This material shows one of the lowest attenuation effects on the propagating acoustic energy. The polybutadiene layer used as materials for the inner layer 47 show an improved acoustic wave transmission (lower attenuation) for the entire acoustic window layer 13. This may be attributed to the different mechanism of the electro-acoustical transformation in the CMUT compared to the PZT. The PZT-based transducer typically has a parallelepiped shape, wherein at least one of its faces is adapted to vibrate in a piston-like motion during the transmission of the acoustic wave. The displacement of the vibrating (active) face is homogeneous throughout the face surface.

Figure 7:
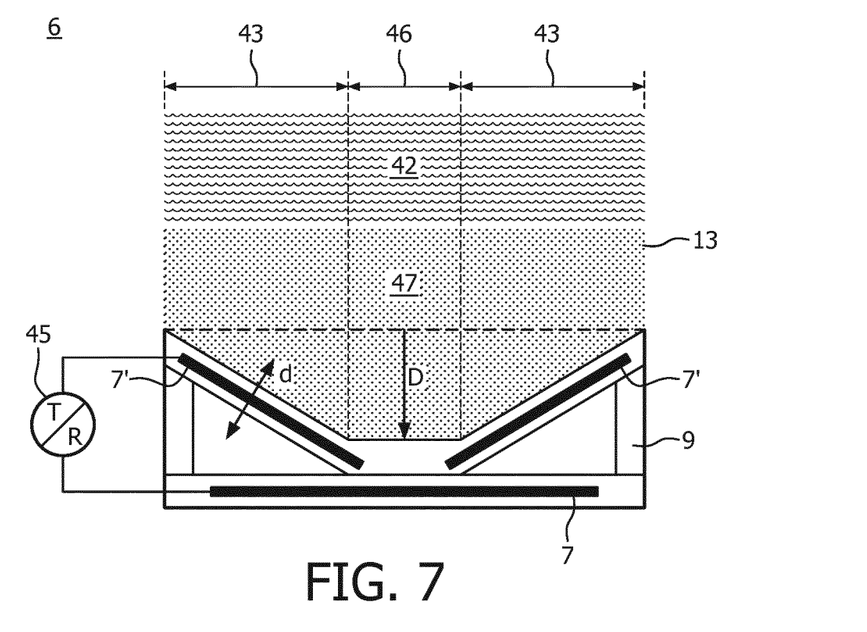
FIG. 7 shows schematically and exemplarily a side view of a CMUT cell operating in the collapsed mode and being acoustically coupled to an acoustic window layer.

In contrast, the CMUT's vibrating membrane has a different displacement throughout the membrane's area (surface). In a conventional operation mode the membrane's displacement is highest in the central part of the CMUT cell and lowest at the periphery of the membrane. In a collapsed mode of operation as shown in FIG. 7 the membrane 5 of the CMUT cell 6 is partially contacting the cell floor, which results in the biggest membrane displacement (D) compared to the conventional operation mode. During the CMUT operation a central part of the membrane 46 may be brought into the contact with (collapsed to) the cell floor by applying a collapsed d.c. voltage value (the d.c. voltage is supplied by the drive circuitry 45). The applied a.c. signal voltage supplied by the drive circuitry 45 causes the suspended portions of the membrane 43 (located at a periphery of the membrane) to move/vibrate under applied electrical signal in between electrodes 7 and 7'. From technology point of view, the CMUT with the collapsed membrane can in principle be manufactured in any conventional way, comprising providing a CMUT with a membrane and applying different means, such as electrical (bias voltage) or pressure, in order to bring the membrane to a collapsed state. In the collapsed operation mode, the displacement D of the central part of the membrane is fixed, while the suspended portions of the membrane vibrate with an amplitude d, which is determined by the a.c. voltage signal for the given CMUT cell design.

The variation in the displacement of the membrane's vibrating portions imposes different requirements on inner layer 47 properties of the acoustic window layer 13 in order to provide an improved acoustic coupling of the operating CMUT transducer. The acoustic window layer may need to adopt its inner surface to the membrane's displacement. The relatively light molecular weight of the polybutadiene combined with its relatively low hardness (below 60 ShoreA, preferably below 50 ShoreA) may provide an improved acoustic contact between the acoustic window layer 13 and the CMUT's membrane adapted to vibrate. In addition the low acoustic wave attenuation of the material forming the inner layer may provide an improved transition of the wave throughout the acoustic layer 13.

Thus this embodiment describes an optimal acoustic window layer design comprising the inner layer 47 of the polyolefin based elastomer and the outer layer 42 of the thermoplastic polymer and the polyolefin elastomer blended in the polymer, wherein the acoustic window layer 13 is provides an optimal operation conditions for the CMUT ultrasound array. Preferably, the array is arranged to operate in the collapsed mode by comprising at least one drive circuit 45 coupled to the CMUT cell 6 and adapted to (a) bring the membrane 5 into a collapsed state in which the membrane is collapsed to the substrate 4, by applying a d.c. voltage over the first 7 and the second electrodes 7' of the at least one CMUT cell, and (b) activate the CMUT cell by applying an a.c. voltage over the first and the second electrodes of the at least one said CMUT cell.

In this mode the CMUT ultrasound array may transmit or receive ultrasound acoustic at different frequencies by varying the applied d.c. voltage, which in return changes the contact area of the membrane 5 with the substrate 4. The larger the d.c. voltage the larger the contact area in the collapsed mode and the higher the resonance frequency of the CMUT cell. Therefore, compared to the PZT-based array the CMUT-based ultrasound array may impose additional requirements into the acoustic window layer in order to have provided optimal acoustic wave propagation for a large frequency range, in which the CMUT ultrasound array is adapted to operate. Therefore, it is desirable to have both the inner 47 and the outer 42 layers showing improved acoustic properties within the broad band of the operating frequencies.

Polybutadiene material has acoustic impedance of about 1.6 MRayl. In order to minimize an impedance mismatch between the ultrasound array and the ultrasonicated tissue it may be desirable to increase the acoustic impedance value of the acoustic window material comprising the polybutadiene. This can be achieved by adding a filler, such as insulating particles 41, into the inner layer 47. The introduction of the insulating particles into the inner layer increases a total density of the first layer. It has been discovered that the additional acoustic losses caused by the embedded insulating particles are sufficiently low and do not considerably influence a quality of the acoustic wave propagation through the polymeric layer.

As an example, Table 1 shows the measured changes in acoustic properties of the polybutadiene layer with the introduction of zirconium dioxide ($ZrO_2$) insulating particles having in average diameter of 2-3 micron and taking a fixed percentage of a total weight of the inner layer.

TABLE 1

Changes in the density, acoustic wave velocity, acoustic impedance and attenuation (at frequency of 7 MHz) with an increasing weight percentage of $ZrO_2$ particles in the total weight of the polybutadiene layer.

| % $ZrO2$ | Density ($g/cm^3$) | Velocity (mm/msec) | Impedance (MRayl) | Attenuation @7 MHz (dB/mm) |
|---|---|---|---|---|
| 0 | 0.906 | 1570 | 1.423 | 0.55 |
| 4% | 0.937 | 1553 | 1.455 | 0.75 |
| 8% | 0.972 | 1532 | 1.489 | 0.87 |
| 16% | 1.0405 | 1503 | 1.564 | 1.05 |
| 24% | 1.0855 | 1469 | 1.5945 | 1.25 |

As can be seen from the table with the total density increase of the first layer comprising polybutadiene, the acoustic impedance of the layer can be tuned towards higher values, e.g. closer to the tissue's acoustic impedance, while the attenuation of the layer still remains below 1.5 dB/mm, even for the layers comprising 25% of its weight taken by the insulating particles ($ZrO_2$). When the first layer of the acoustic window layer, comprising the polymeric material with embedded insulating particles, has a density equal or above 0.94 $g/cm^3$ and an acoustic impedance equal or above 1.5 MRayl a direct acoustical coupling of the acoustical window layer to the membrane of the CMUT cell is provided. Thus, no additional coupling medium between the acoustic window and the CMUT array is required. Moreover, the acoustic impedance equal or above 1.5 MRayl matched closer to the values in between the CMUTs acoustic impedance and the outer layer 42.

The advantage of the light molecular weight thermoset rubbers is that compared to commonly used in ultrasound silicon based rubbers (filled silicon), these thermoset rubbers, in particular polybutadiene, possess higher acoustic impedance. Therefore, in order to tune the acoustic impedance of the polyolefin based polymeric layer to a tissue's impedance a relatively smaller amount of the filler may be used in this polymeric material, compared to the filled silicones. Since an introduction of the insulating particles to a layer on average increases its hardness, an application of the polymeric materials (thermoset rubbers) having higher acoustic impedance provides the acoustic window layer 13 with relatively smaller changed hardness (remaining below 60 ShoreA, preferably below 50 ShoreA) and a considerably lower attenuation (preferably below 1.5 or 2 dB/mm) than with filled silicones. In order to bring the acoustic impedance of the filled silicon closer to the soft tissue's impedance, i.e. from 1.1 MRayl to 1.6 MRayl, a larger amount of the filler particles is required. This introduction of the particles introduces considerable attenuation and increases the hardness of the filled silicon layer.

An optimum acoustical coupling of the acoustical window layer to the membrane of the CMUT cell can be provided by a combination of the thermoset rubber having low attenuation and acoustic impedance above 1.4 MRayl; and a relatively constant hardness of the first layer with an introduction of the embedded insulating particles.

In an embodiment of the present invention it may be beneficial in using ceramic particles as the insulating particles. Ceramic particles, such as metal oxides ($ZrO2$, $Al2O3$, $TiO2$, $Bi2O3$, $BaSO4$, etc.) show high insulating properties, which may be advantages in providing additional insulation to the arrays electronics. Moreover, there are multiple ways developed in the art for manufacturing ceramic particles of a well-defined size.

The reduced acoustic wave attenuation in the layers of polybutadiene and polybutadiene having 25% of the layer's total weight filled with $ZrO_2$ particles can be seen from the curves 85 and 85 in FIG. 3 respectively. The polybutadiene with embedded insulating particles shows attenuation below 2 dB/mm at 10 MHz and below 1 dB/mm at 5 MHz.

Therefore, a combination of the inner layer 47 comprising the polyolefin elastomer and the outer layer 42 comprising the polymer blend in accordance with the principles of the present invention provides the acoustic window layer with improved acoustic properties, wherein the acoustic window layer is also mechanically and chemically resistant to the medical disinfectants. The acoustic properties of the inner and the outer layers can be further adjusted by varying the weight ratios of the embedded insulating particles the blend component.

Figure 6:
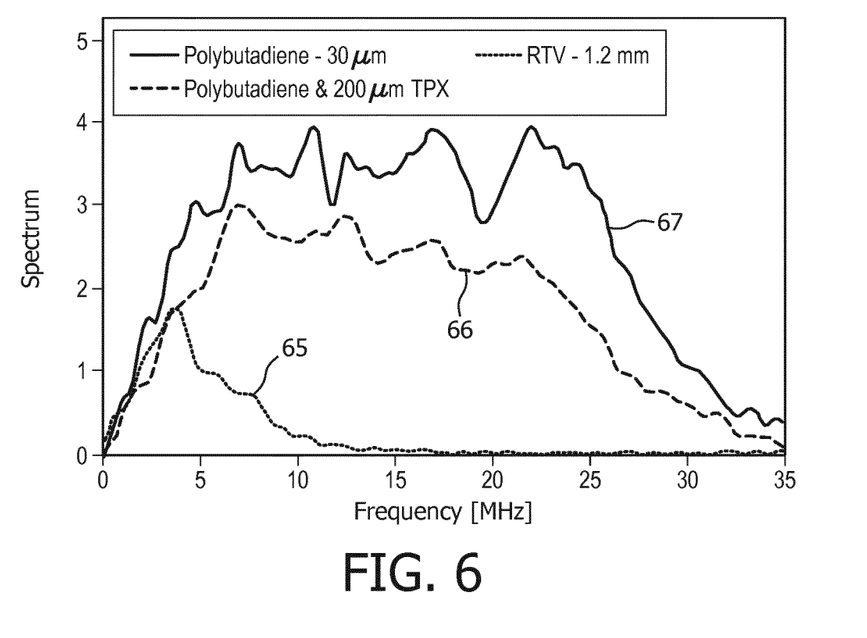
FIG. 6 shows comparison of an output pressure of the ultrasound array comprising an acoustic window layers having different materials forming the outer and inner layers.

FIG. 6 shows an output pressure (MPa) in the frequency range from 0 up to 35 MHz for the CMUT ultrasound array comprising an acoustic window layers 13 having different materials. Curve 65 corresponds to the ultrasound array overlaid by the filled silicon rubber (RTV) of 1.2 millimeter in thickness. As can be seen the silicon rubber layer has poor performance for the CMUT array in this range of frequencies manifesting in the low output pressure reaching its maximum of 1.5 MPa around 5 Mhz; beyond frequencies of 7 MHz the filled silicon rubber exhibits a strong attenuation of the acoustic signal. The CMUT array overlaid by the first layer comprising polybutadiene material (curve 67) having a thickness of 30 micrometer shows an ultra-wide bandwidth with an output pressure reaching as high as 3.5 MPa. Curve 66 corresponds to the acoustic window layer 13 comprising both the inner layer 47 formed by polybutadiene (30 micrometer thick) and the outer layer 42 formed by a blend of the polymethylpentene and polyolefin elastomer, wherein the outer layer has a thickness of 200 micrometer. The output pressure for this array reaches as high as 2.5 MPa and is above 2 MPa in a broad frequency range from 7 up to 5 MHz. Thus, presence of the outer layer 47 provides the ultrasound probe with the wide frequency bandwidths, characterized with low acoustic wave attenuation, combined with the durable and cleanable outer surface 71.

An additional advantage of the outer layer 47 comprising the polyolefin based thermoplastic polymer and polyolefin based elastomer blended therein is the blend is moldable and can be easier adapted to an industrial application as an acoustic window/lens material in the ultrasound probes.

Figure 9:
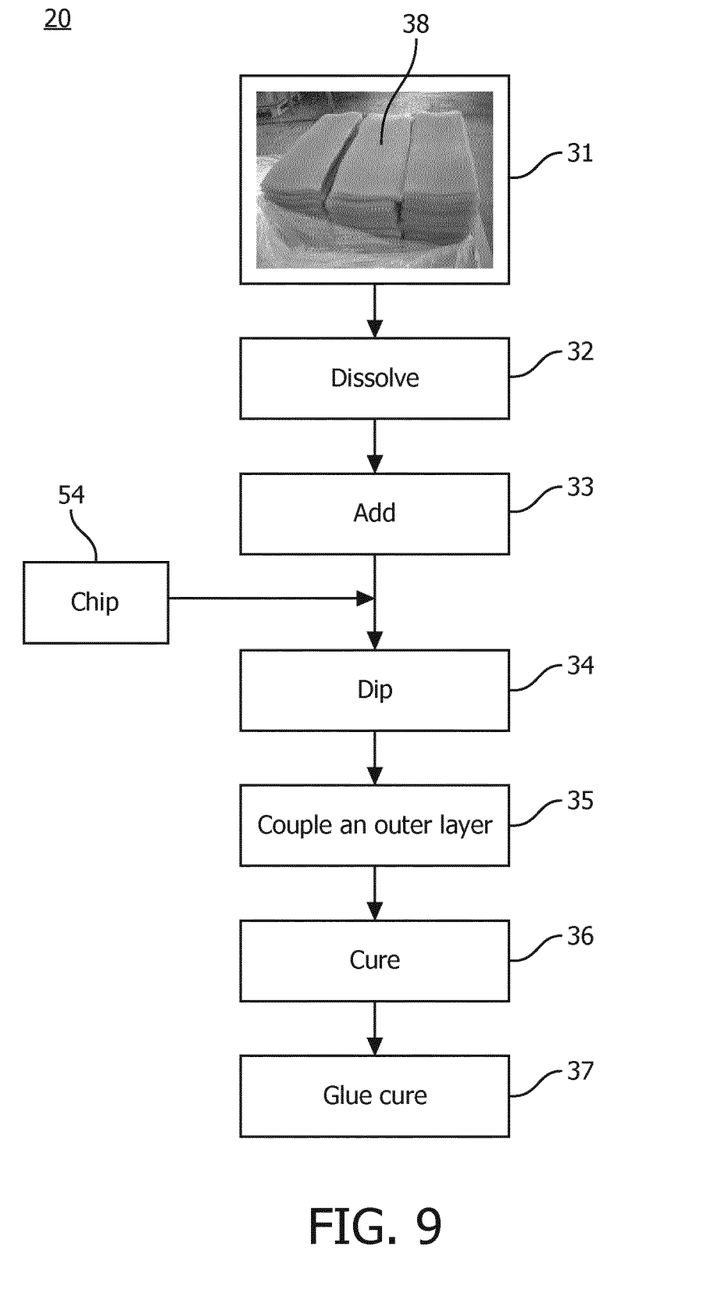
FIG. 9 schematically illustrates a method for manufacturing an ultrasound array in accordance with the present invention.

An industrial application of the polymeric materials as layers is described. In FIG. 9 method 20 for manufacturing an ultrasound array comprising the acoustic window layer in accordance with the present invention is illustrated. A granulate of pre-polymerized polybutadiene 38 (CB728T from Lanxess) is provided in step 31. In step 32 the block is granulated and dissolved in solvents like alkanes, branched or cyclic alkanes, for example hexane, heptane, cyclohexane. In step 33 the optimization of the acoustic impedance of the inner layer can be achieved by adding insulating particles to the solvent, wherein the polymeric material act as a dispersion agent for the particles, such that a liquid mixture of the polymeric material and the insulating particles is provided. The additional dispersion agents like fatty acids (a carboxylic acid with an aliphatic chain, which is either saturated or unsaturated) may be added in the liquid mixture. The filler particles in the liquid mixture may increase the hardness of the inner layer of the acoustic window, while fatty acids may counter play this hardness increase keeping the average hardness of the first layer at the relatively constant value. The unsaturated chains of fatty acid like oleic acid, linoleic acid and linolenic acid (one, two and respectively tree double carbon bonds) can polymerise and bond to the polybutadiene chains. This provides a good dispersion/distribution of particles in the liquid mixture. In step 54 a chip having the ultrasound array with at least one CMUT cell coupled to an integrated circuitry is provided. In step 34 the chip is dipped in the liquid mixture, such that a layer comprising the liquid mixture overlays the CMUT cell. Since in step 33 a minimum impedance mismatch between the liquid mixture and the propagating medium can be achieved, the tolerance to the thickness variation of the liquid mixture layer is rather high. The increase in the dipping time would increase the thickness of the liquid mixture layer. In the step 35 the chip with the liquid mixture layer may be let drying at elevated temperature of about 70° C. With the time, when the solvent starts evaporating from the liquid mixture, the liquid mixture layer may become more solid (sticky). At this stage the outer layer of the polyolefin thermoplastic with the polyolefin elastomer blended therein can be applied to the liquid mixture layer. The advantage of this step is that the outer layer can be coupled to the first layer without any glue.

The preferred weight ratio of the polyolefin elastomer in the blend of the thermoplastic polyolefin is below 40%. For the embodiment describing polymethylpentene (TPX) with polyolefin elastomer blended therein (Engage), the elastomer's weight ratio increase beyond 40% introduces too high attenuation in the outer layer. Below 40% an optimal balance between the decreased acoustic impedance, reduced shear wave propagation and increased acoustic wave attenuation is achieved. The preferred weight ratio of the polyolefin elastomer in the thermoplastic polyolefin blend is in between 10% and 30%, in particular in between 15% and 20%. The exact value of the selected weight ratio may depend on the medical application of the ultrasound array. For example, for low frequency applications (below 5 MHz) a relatively higher weight ratio may be selected (above 25-30%) since the outer layer's attenuation may be below 2 dB/mm. In a higher frequency range (in between 5 MHz and 10 MHz), in order to keep the attenuation below 2 dB/mm, the lower weight ratio of the polyolefin elastomer in the blend may be selected, such as 15%-20%.

Further, in step 36 the layer overlaying the CMUT cell is cured at a temperature sufficient to evaporate the remaining solvent (about 100° C., in the case of heptane) from the liquid mixture layer, such that an acoustic window layer 13 comprising a polymeric material 47 with insulating particles 41 embedded therein is provided overlaying the CMUT cell. Alternately, to assure a better fixation the outer layer may be coupled to the inner layer with the third layer of glue and further cured in step 37.

This method can be advantageously applied on industrial scale owing to the simplicity of the steps and large tolerance of the ultrasound array's performance to the acoustic layer window thickness. The layer thickness can be increased by repeating the steps of dipping 34 and drying 36. Due to the possibility of the impedance optimization in steps 33 and 35 low attenuation properties of the polyolefin materials, a local thickness deviation in the acoustic window layer from the average value can be higher than the accepted standard in commonly used spray or spin coat manufacturing. In addition to this manufacturing method provides flexibility in different chip designs and electrical contact bonding implemented in the array.

The method can be also beneficially used for different chip size, especially in the area miniaturized ultrasound arrays, such as interventional devices and catheters.

FIG. 8 illustrates the principle design of an ultrasonic imaging system 202.

The ultrasound imaging system is generally denoted with reference numeral 202. The ultrasound imaging system 202 is used for scanning an area or volume of the body, e.g. of a patient 201. It is to be understood that the ultrasound system 202 may also be used for scanning other areas or volumes, e.g. body parts of animals or other living beings.

For scanning the patient 201, an ultrasound probe 200 may be provided. In the embodiment shown, the ultrasound probe 200 is connected to a console device 203. The console device 203 is shown in FIG. 8 as a mobile console. This console 203 may, however, also be realized as a stationary device. The console device 203 is connected to the probe 200 via an interface 206 formed in a wired manner. Further, it is contemplated that the console device 203 may also be connected to the probe 200 in a wireless manner, for example using UWB transmission technology. The console device 203 may further comprise an input device 205. The input device may have buttons, a key pad and/or a touchscreen to provide an input mechanism to a user of the ultrasound imaging system 202. Additionally or alternatively, other mechanisms may be present in the input device 205 to enable a user to control the ultrasound imaging system 202.

Further, the console device 203 comprises a display 204 to display data generated by the ultrasound imaging system 202 to the user. By this, the volume within the patient 201 that is scanned via the ultrasound probe 200 can be viewed on the console device 203 by the user of the ultrasound system 200.

The ultrasound probe 200 comprises the CMUT transducer array constructed in accordance with the present invention.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. An acoustic window layer for an ultrasound array, which layer has an inner surface arranged to face the array and an outer surface arranged to face a patient, and comprising
an outer layer comprising a thermoplastic polymer polymethylpentene and an elastomer selected from the polyolefin family (POE) blended therein, wherein the outer layer is located at the outer surface of the acoustic window layer.

2. The acoustic window layer according to claim 1, wherein the selected elastomer is a copolymer.

3. The acoustic window layer according to claim 2, wherein the selected elastomer is a thermoplastic elastomer (TPE).

4. The acoustic window layer according to claim 3, wherein the copolymer has a first monomer being an alpha olefin and a second monomer being ethylene.

5. The acoustic window layer according to claim 4, wherein the first monomer is octane.

6. The acoustic window layer according to claim 3, wherein the outer layer exhibits a first glass transition temperature below −40 centigrade Celsius and a second glass transition temperature in between 0 and 50 centigrade Celsius.

7. The acoustic window layer according to claim 1, wherein a weight ratio of the elastomer blended in the outer layer is between 30% and 40%.

8. The acoustic window layer according to claim 7, wherein the weight ratio of the elastomer blended in the outer layer is in between 15 and 20%.

9. The acoustic window layer according to claim 1, wherein the outer layer exhibits an acoustic impedance in between 1.5 to 1.6 MRayl and an acoustic loss per millimeter for acoustic energy of a shear wave equals or is above 3 dB.

10. The acoustic window layer according to claim 1, wherein the outer layer has a density in between 0.8 and 0.85 g/cm$^3$ and acoustic wave velocity in between 2000 and 1900 mm/msec.

11. The acoustic window layer according to claim 1, wherein the outer layer exhibits a first melting point (MP1) in between 30 and 70 centigrade Celsius and a second melting point (MP2) in between 200 and 250 centigrade Celsius.

12. The acoustic window layer according to claim 1, wherein the acoustic window layer further comprises an inner layer located at the inner surface of the acoustic window layer, wherein the inner layer comprises a thermoset rubber.

13. An ultrasound probe comprising the acoustic window layer according to claim 1 and an ultrasound transducers array, wherein an emitting side of the ultrasound array is acoustically coupled to the inner surface of the acoustic window layer.

14. The ultrasound probe according to claim 13, wherein the ultrasound transducer array comprises at least one capacitive micro-machined ultrasound transducer (CMUT) cell, wherein the CMUT cell comprises a substrate having a first electrode; a cell membrane having a second electrode, which opposes the first electrode with a cavity there between, wherein the membrane is arranged to vibrate upon cell activation.

15. The ultrasound probe according to claim 14, wherein the ultrasound transducer array further comprising at least one drive circuit coupled to the cell and adapted to (a) bring the membrane into a collapsed state in which the membrane is collapsed to the substrate, by applying a d.c. voltage over the first and the second electrodes of the at least one CMUT cell, and (b) activate the CMUT cell by applying an a.c. voltage over the first and the second electrodes of the at least one said CMUT cell.

* * * * *